(12) United States Patent  
Spelman et al.

(10) Patent No.: US 6,374,670 B1
(45) Date of Patent: Apr. 23, 2002

(54) NON-INVASIVE GUT MOTILITY MONITOR

(75) Inventors: Francis A. Spelman; Page Read; N. Mani Prakash; James A. Nelson; Charles E. Pope; Margaret Heitkemper; James D. Rothermel, all of Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 08/402,872

(22) Filed: Mar. 13, 1995

(51) Int. Cl.$^7$ .................................................. A61B 5/22
(52) U.S. Cl. ..................................................... 73/379.01
(58) Field of Search .......................... 73/379.01, 865.4; 128/780, 782, 10

(56) References Cited

U.S. PATENT DOCUMENTS

| | | | |
|---|---|---|---|
| 1,971,189 A | * 8/1934 | Leibing | 324/67 |
| 3,005,458 A | * 10/1961 | Brook et al. | 600/12 |
| 3,961,632 A | * 6/1976 | Moosun | 600/12 X |
| 4,269,826 A | * 5/1981 | Zimmerman et al. | 600/12 X |
| 4,303,062 A | * 12/1981 | Vars | 600/12 |
| 4,809,713 A | * 3/1989 | Grayzel | 128/785 |
| 5,057,095 A | * 10/1991 | Fabian | 600/12 X |
| 5,125,888 A | * 6/1992 | Howard et al. | 600/12 |
| 5,247,938 A | * 9/1993 | Silverstein et al. | 128/662.03 |
| 5,425,382 A | * 6/1995 | Golden et al. | 128/899 |

FOREIGN PATENT DOCUMENTS

SU 1174021 * 8/1985 ................. 128/780

OTHER PUBLICATIONS

"Magnetic Markers as a Noninvasive Tool to Monitor Gastrointestinal Transit," by W. Weitschies et al., IEEE Transactions on Biomedical Engineering, Vo.41, No. 2, Feb. 1994, pp. 192–195.

"Measurement of Gastrointestinal Transit Time by Means of Biomagnetic Instrumentation: Preliminary Results," M.A. Macri et al., Clin. Phys. Physiol. Meas., vol. 12, Supp. A, 1991, pp. 111–115.

* cited by examiner

Primary Examiner—Benjamin R. Fuller
Assistant Examiner—Jewel V. Thompson
(74) Attorney, Agent, or Firm—Glenn D. Bellamy

(57) ABSTRACT

An apparatus (4) and method of non-invasive monitoring of gut motility. An ingestible magnet (10, M) is swallowed by the patient (12) and then linear and rotational movement is directionally detected by an external compass (14, 16). In preferred form, movements of the magnet (10, M) are recorded by a memory means (18) and graphically presented (20) over a period of predetermined time. An alternate embodiment includes multiple compasses (C1, C2) for directionally locating the magnet (10, M) within the patient (12).

14 Claims, 2 Drawing Sheets

NON-INVASIVE GUT MOTILITY MONITOR

GOVERNMENT RIGHTS

This invention was made in part with government support under Grant No. RR001663-33, awarded by the National Institutes of Health. The government may have certain rights in the invention.

TECHNICAL FIELD

This application relates to a non-invasive apparatus for and method of monitoring gut motility. In particular, it relates to such an apparatus and method which utilizes a swallowed magnet which can be monitored externally by an electronic flux-gate compass. Gut motility is indicated by linear and rotational movement of the magnet measured by the external compass.

BACKGROUND OF THE INVENTION

The gut is a hollow organ that extracts nutrients and water from food as it is transported from the mouth to the rectum. The muscles of the gut are arranged as longitudinal and circumferential layers. They contract under mechanical, autonomic and humoral control so as to transport and mix their contents by moving them alternately in a forward and reverse direction. This transport and mixing is generally termed "gut motility."

Over 22,000,000 patients in the United States have presented physicians with unexplained bowel symptoms, such as constipation, diarrhea or abdominal pain. Chronic gastrointestinal disorders may result from conditions brought on by diabetes or a variety of symptoms generally labeled as "irritable bowel syndrome" (IBS). Patients suffering from IBS are given a series of gastroenterological and radiological tests to diagnose disease and assess gut function. Because the presently-available diagnostics are relatively expensive and uncomfortable, patients usually go through a barrage of tests to rule out other known diseases or disorders prior to undergoing tests that heretofore were best for assessing abnormal gut motility.

The most commonly-used diagnostic tool, orogastric manometry, is usually used only after other less invasive and less costly procedures have been exhausted due to the high cost and patient discomfort/intolerance associated with orogastric manometry. Orogastric manometry has previously provided the most quantitative assessment of upper gastrointestinal muscular function and disorder but can provide information about the action of only the esophagus, stomach, duodenum and perhaps the first six inches of the proximal bowel, known as the duodenojejunal flexure.

Anal manometry provides information about the descending colon, sigmoid colon and rectum. Neither manometry technique provides data about the condition of the ileum (small intestine) or the ascending and transverse colon of the large intestine, which together comprise the major volume of the alimentary canal.

Manometry requires that a long tube be inserted into the digestive tract and remain in place for times which vary from five hours for a routine diagnosis to twenty-four hours for a definitive assessment. Portable manometers have been designed for ambulatory use, but require the application of multiple pressure transducers placed within the gut, and that the orogastric tube be in place during "normal" activity. Stress and discomfort caused to the patient by insertion of the manometric probe can make measurement during "normal" activity difficult. Furthermore, such testing may be virtually intolerable if the patient is even moderately ill. The availability of better non-invasive methods for the diagnosis of disorders of motility and transport would greatly facilitate their management.

Two non-invasive biomagnetic techniques are known to the inventors to have been used to determine gut motility. The first measures the magnetic fields produced when the smooth muscles of the gut contract, producing electrical currents. The other measures the variation in strength of the magnetic fields produced by magnetic particles ingested and moved through the gut naturally. The Superconducting Quantum Interference Device (SQUID) measures minuscule magnetic fields and has been used to monitor both the biomagnetic signals produced by the gut muscles and the changing fields produced by magnetic sources ingested and moving through the gut. Although the SQUID magnetometer is extremely sensitive, it is also quite expensive to purchase and operate. SQUID sensors operate at liquid helium temperatures and must be housed in a liquid helium filled, vacuum-insulated chamber. Most SQUID sensors operate within magnetically-shielded enclosures. While some SQUID sensors are capable of being operated in open rooms, they are still extremely expensive. Multi-sensor devices are even more expensive. Moreover, the need for a magnetically-shielded room would create even greater expense.

SQUID magnetometers have been used in conjunction with ingested slurries of magnetic material to measure gut motility by monitoring the changes in magnetic field strength produced by the moving slurries. This technique requires less sensitivity than the technique of measuring biomagnetic fields produced by the contraction of the smooth muscles. In either case, the SQUID monitor requires that patients remain supine for the duration of the measurements.

The measurement of gut motility frequency is an important component of the diagnosis of gut motility disorders. Specifically, the pattern of frequencies measured is different in normal versus abnormal motility cases. The frequencies measured in normal cases are a function of location along the alimentary canal, ranging from relatively high frequencies (11 per minute) in the duodenum, to low frequencies (6 per minute) in the colon. The frequencies measured are apt to be varied by the feeding state of the patient, as well as other factors.

SUMMARY OF THE INVENTION

This invention provides both an apparatus for and method of measuring gut motility. The apparatus provided is non-invasive and comprises a magnet sized to be ingestible by a patient along with a compass external of the patient directionally sensitive to movement of the magnet in the patient's abdomen for monitoring of gut motility. In preferred form, the compass is an electronic flux-gate compass having an electronic directional output. This output may be stored in either internal or external memory and may be graphically recorded and displayed over a predetermined period of time.

Also in preferred form, use of a sufficiently long, but still ingestible, magnet will cause the device to be sensitive to rotational, as well as linear, movement within the patient's gut. Use of multiple compass detectors will enable location, as well as movement, to be determined, if desired.

The method of the present invention for measuring gut motility in a patient includes the steps of the patient swallowing an ingestible magnet, providing a compass external of the patient's abdomen for directionally sensing movement of the magnet in the patient's abdomen, and monitoring gut motility with the compass by measuring movement of the magnet.

In preferred form, the compass is an electronic flux-gate compass having an electronic output that may be recorded in internal or external memory and graphically displayed over a predetermined period of time. Use of an elongated magnet and the provision of multiple compasses, as described above, is another aspect of the present method.

Close study of the prior art described in the background of the invention section above should be carefully studied in order to put the present invention into proper perspective. Careful reading of the best mode for carrying out the invention and figures of the drawing, all of which are incorporated by reference into the disclosure of this invention, will reveal other aspects and features.

BRIEF DESCRIPTION OF THE DRAWINGS

Like reference numerals are used to indicate like parts throughout the various figures of the drawing, wherein.

BEST MODE FOR CARRYING OUT THE INVENTION

Figure 1:
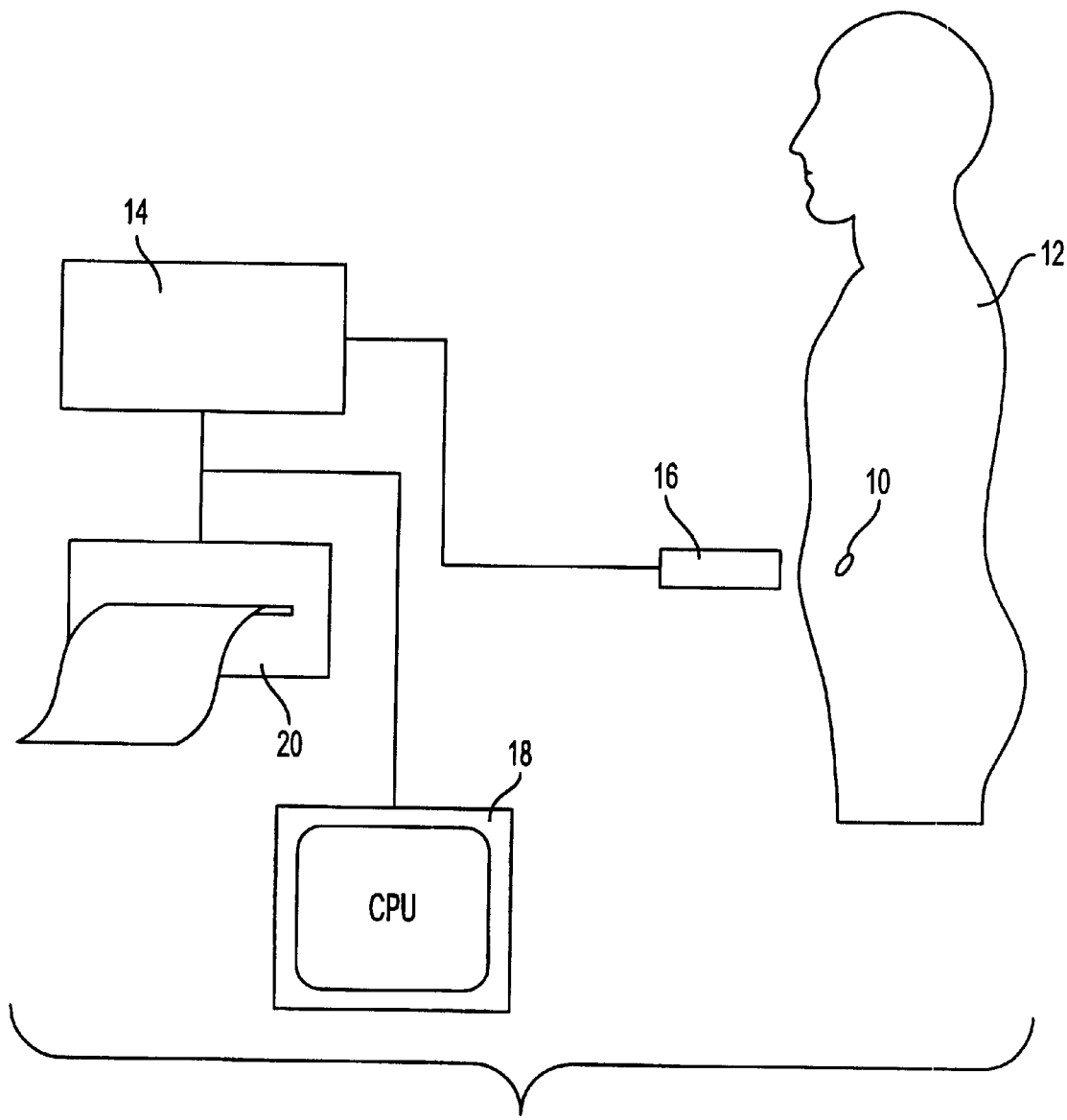
FIG. 1 is a schematic representation of a system according to the preferred embodiment of the present invention.

The present invention provides an apparatus for and method of monitoring gut motility that is non-invasive, inexpensive and allows the patient to be ambulatory. Referring to FIG. 1, an ingestible magnet 10 is swallowed by a patient 12. Any magnet that is sufficiently small to be swallowed and has a magnetic field strength sufficient to influence a compass of ordinary sensitivity at a range of a few inches through body tissue may be used. An ordinary Teflon®-coated stirring magnet has been successfully employed by the inventors.

The position of the magnet 10 may be directionally located by a flux-gate compass 14 having a probe 16 placed in external proximity to the patient's abdomen. An ordinary personal electronic compass will usually have a display which indicates direction relative to the magnetic north pole of the Earth. This display output is usually a digital reading along a circle of 360°, or increments thereof. When the detection probe 16 of the compass 14 is placed within proximity of the ingested magnet 10, the flux-gate compass is effectively swamped by the magnetic field of the ingested magnet 10 and no appreciable background interference is created by the Earth's magnetic field.

Because the variation of the ingested magnet's position over a period of time is essential to diagnosis of gut motility disorders, automated monitoring of the magnetic direction by a computer 18 and output recorder 20 is highly desirable. An inexpensive flux-gate compass can be modified to be the sensor of the portable monitor and has been successfully done by the inventors in experimentation. The gut motility monitor of the present invention measures the changes in the relative direction of the magnet 10 from the sensor 16, as measured by the flux-gate compass 14.

It is expected that the computer monitoring device 18 need store only about 1.5 megabytes to acquire ten samples per second, each sample comprising about 1.5 bytes, from the compass 14 for twenty-four hours. This task can be accomplished easily with a battery-powered digital controller of well-known construction with modest internal or external memory. The controller 18 will not have to be particularly fast relative to well-known technology of today, since a sample rate of ten per second is low. Power consumption is expected to be minimal so that the controller 18 and compass 14 may be powered by small batteries. In preferred form, the controller 18 will acquire data from the flux-gate compass 14 and then pass the data to a central work station for printed output 20 at the end of a study. The time-varying directional readout can be subjected to additional signal processing to extract salient features, if desired. For example, frequency analysis of the signal (Fourier analysis) or FFT (Fast Fourier Transform) may be employed.

The sensor 16 may be held by a belt on the abdomen. As the magnet 10 moves through the alimentary canal, motility can be monitored for each portion of the organ. Because the device requires no intubation or confinement to a hospital bed, the patient 12 may be ambulatory and gut motility monitoring could be performed at home or in the workplace at a substantial reduction in health care costs and an increase in patient comfort.

Figure 2:
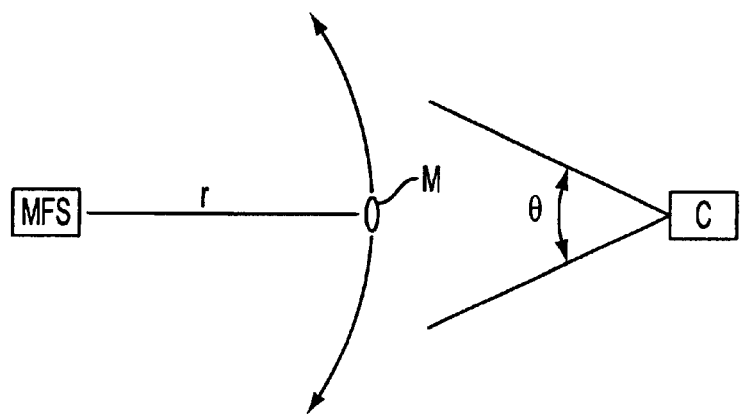
FIG. 2 is a schematic representation comparing the measurements of a flux-gate compass to a magnetic field strength detector.
Figure 3:
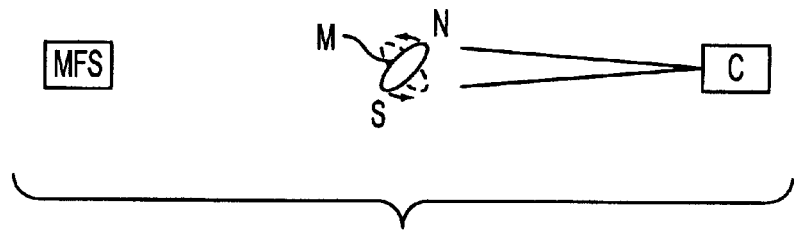
FIG. 3 is another schematic drawing representing another distinction between the detection of a flux-gate compass and a magnetic field strength detector.
Figure 4:
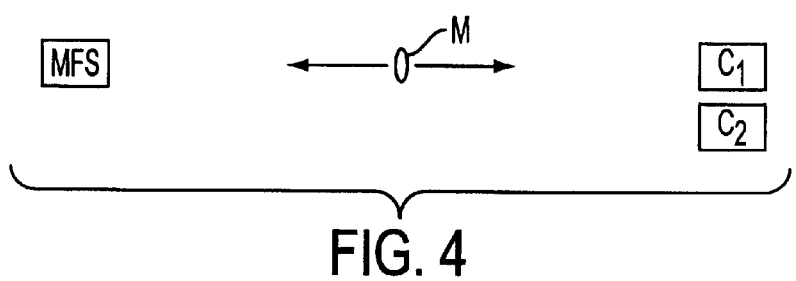
FIG. 4 is a schematic drawing comparing yet another distinction between the detection of one or more flux-gate compasses and a magnetic field strength detector.

Referring now to FIGS. 2–4, virtually every movement of the magnet M may be detected and monitored by the compass C of the present invention. The inventors found this to be less true with respect to a magnetic field strength (MFS) magnetometer. For example, referring to FIG. 2, if the magnet M moves along an arcuate path at a distance r from the MFS, the movement would be undetected because magnetic field strength would not be varied. Similar movement, however, would be detected by the compass of the present invention because of the relative change in direction along angle θ.

Referring to FIG. 3, rotational movement of the magnet M, even though significant linear movement is absent, would easily be detected by the compass C of the present invention. This is notably so due to the shifting or reversal of the magnetic north and south poles. This type of movement may be detected, but to a lesser extent, by a MFS monitor. If detection of this rotational movement is deemed important, a magnet having north and south poles spaced apart a sufficient distance should be used such that this movement is easily detected by the compass C. The physical distance between the poles can be quite minute without losing detectability. Thus, providing a magnet that is sized to be easily ingested does not create a problem in carrying out the present invention.

Referring to FIG. 4, linear movement of the magnet M directly toward and away from a detector probe would be better monitored by an MFS magnetometer than by a single compass C1. This is true because magnetic field strength would be varying with such linear movement, while direction relative to the detector would not. Linear movement of this type, however, would be fully recordable by utilizing a spaced-apart pair of compasses C1, C2 according to an alternate embodiment of the present invention. This is not considered to be a significant impairment of the present invention, as movement of this type would be limited to an insignificant portion of a diagnostic procedure lasting several hours.

Figure 5:
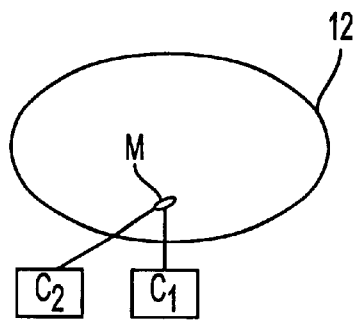
FIG. 5 is a schematic representation showing the location of an ingested magnet within a transverse section of a patient by a pair of flux-gate compasses.

Referring to FIG. 5, as described above, a single compass C1 of the present invention is completely adequate if only motility is to be monitored. If exact position, for determining location along the alimentary canal, is desired, two or more compasses C1, C2 may be employed to "triangulate" the location of the magnet M within the abdomen of a patient 12.

The inventors are not aware of any prior devices using a flux-gate compass to determine the relative direction of an ingested magnet for measurement of gut motility. Prior biomagnetic techniques are not known to measure variation in relative direction of an ingested magnet from the sensor for gut motility monitoring. Since IBS has been diagnosed by exclusion, this new device and method will likely provide seminal new information for both diagnosis and therapy. It is also expected to provide an improved way of obtaining information about diabetic patients who suffer from myopathic/neuropathic disorders which severely compromise gut motility.

The apparatus for a method of monitoring gut motility described above represents merely an example of how the present invention may be used. Of course, many variations to the apparatus and steps of the method may be altered without departing from the spirit and scope of the present invention. For this reason, patent protection is not intended to be limited by these preferred embodiments, but instead, only by the following claim or claims construed according to accepted doctrines of claim interpretation, including the doctrine of equivalents and reversal of parts.

What is claimed is:

1. An apparatus for non-invasive monitoring of gut motility in a patient, comprising:
    a magnet sized to be ingestible by the patient;
    a compass external of the patient directionally sensitive to movement of the magnet in the patient's abdomen for monitoring of gut motility according to movements of the ingested magnet.

2. The apparatus of claim 1, wherein the compass is an electronic flux-gate compass having an electronic directional output.

3. The apparatus of claim 2, further comprising a memory means for recording detected movements of the magnet over a predetermined period of time.

4. The apparatus of claim 2, further comprising a recorder for providing a graphic record of the magnet's movement over a predetermined period of time.

5. The apparatus of claim 1, further comprising a recorder for providing a graphic record of the magnet's movement over a predetermined period of time.

6. The apparatus of claim 1, wherein the magnet has poles spaced apart a sufficient distance such that the compass will measure rotational movement of the magnet within the patient's gut.

7. The apparatus of claim 1, further comprising at least a second compass external of the patient directionally sensitive to movement of the magnet in the patient's abdomen for calculating location of the magnet within the patient.

8. A method of measuring gut motility in a patient, comprising the steps of:
    the patient swallowing an ingestible magnet;
    providing a compass external of the patient's abdomen for directionally sensing movement of the magnet in the patient; and
    monitoring gut motility with the compass by measuring movement of the magnet within the patient.

9. The method of claim 8, wherein the compass is an electronic flux-gate compass having an electronic directional output.

10. The method of claim 9, further comprising the step of recording movements of the magnet sensed by the compass over a predetermined period of time.

11. The method of claim 9, further comprising the step of providing a graphic recorded output of the magnet's movement over a predetermined period of time.

12. The method of claim 8, further comprising the step of providing a graphic recorded output of the magnet's movement over a predetermined period of time.

13. The method of claim 8, wherein the magnet has poles spaced apart a sufficient distance such that the compass will measure rotational movement of the magnet within the patient's gut.

14. The method of claim 8, further comprising the step of providing at least a second compass external of the patient's abdomen for, in conjunction with, the first compass, directionally sensing location of the magnet in the patient.

* * * * *